(12) United States Patent
Godwin et al.

(10) Patent No.: US 6,355,711 B1
(45) Date of Patent: Mar. 12, 2002

(54) HIGH PERFORMANCE PLASTICIZERS FROM BRANCHED OXO ALCOHOLS

(75) Inventors: Allen David Godwin, Seabrook; Dwight McLean Lyman, Houston, both of TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/282,992

(22) Filed: Mar. 31, 1999

Related U.S. Application Data
(60) Provisional application No. 60/082,813, filed on Apr. 23, 1998.

(51) Int. Cl.[7] .............................. C08K 5/09; C07C 67/36
(52) U.S. Cl. .................... 524/285; 524/287; 524/306; 524/311; 524/296; 524/297; 524/315; 524/318; 560/97; 560/233
(58) Field of Search ................................ 524/296, 297, 524/285, 287, 306, 311, 315, 318; 560/233, 97

(56) References Cited

U.S. PATENT DOCUMENTS

| | | | |
|---|---|---|---|
| 3,056,818 A | 10/1962 | Weber | 260/410.6 |
| 4,291,127 A | 9/1981 | Akabayashi et al. | 560/76 |
| 4,543,420 A | 9/1985 | Godwin et al. | 560/76 |
| 4,675,463 A | * 6/1987 | Gilvicky et al. | 584/514 |
| 5,072,057 A | * 12/1991 | Oswald et al. | 568/840 |
| 5,661,204 A | 8/1997 | Bahrmann et al. | 524/296 |

OTHER PUBLICATIONS

"The Nonyl Phthalate Ester and Its Use in Flexible PVC," Brian L. Wadey, Lucien Thil, Mo A. Khuddus and Hans Reich, Journal of Vinyl Technology, Dec. 1990, vol. 12, No. 4, pp. 208–211.

* cited by examiner

*Primary Examiner*—Peter D. Mulcahy
(74) *Attorney, Agent, or Firm*—Paul T. Lalbie

(57) ABSTRACT

A plasticizer ester prepared from the catalytic reaction of (1) at least one branched $C_7$–$C_{11}$ oxo alcohol prepared from $C_6$–$C_{10}$ olefins via hydroformylation and having at least 50% methyl branching at the beta carbon, and (2) at least one acid or anhydride.

17 Claims, 2 Drawing Sheets

HIGH PERFORMANCE PLASTICIZERS FROM BRANCHED OXO ALCOHOLS

This application claims benefit to U.S. provisional application Ser. No. 60/082,813, filed Apr. 23, 1998.

FIELD OF THE INVENTION

The present invention is directed primarily to a series of plasticizer esters and method for making such esters for use in the formulation of polyvinyl chloride (PVC), such as phthalates, adipates and trimellitates. These plasticizer esters are prepared by the reaction of an aromatic or aliphatic diacid, triacid, or acid anhydride with an alcohol prepared by the hydroformylation of a $C_6$–$C_{10}$ olefins using a titanium, zirconium or tin-based catalyst or an acid catalyst, provided that the olefin contains at least 50% mono methyl branching at the beta carbon, e.g., 2-methyl octene-1 or 2-methyl octene-2. Such novel plasticizers have been found to be especially useful in the manufacture of low fogging, flexible polyvinyl chloride (PVC) automotive interior trim applications.

BACKGROUND OF THE INVENTION

Since their introduction in the late 1960's, esters of branched $C_9$ alcohols have continued to gain prominence as plasticizers for PVC. PVC compounds prepared with phthalate esters of branched $C_9$ alcohols are used in many different market segments; these include electrical wire insulation, flexible vinyl flooring, vinyl coated wallpaper, vinyl shower curtains, synthetic leather, vinyl boat covers, vinyl swimming pool liners, vinyl stationary products or notebook covers, and tarpaulins.

Esters of branched $C_9$ alcohols are preferred over esters prepared from 2-ethylhexanol, because when used in PVC compounds, the $C_9$ esters yield performance advantages over the $C_8$ esters in higher performance, improved extraction resistance to water, lower emissions during processing, lower specific gravity, and low temperature flexibility. However, these products are slightly defensive to the $C_8$ esters in that they require 1° C.–3° C. higher processing temperatures and slightly longer dry-blending times.

Although the $C_9$ esters offer advantages over the $C_8$ esters with lower emissions, the level of emission are often not acceptable for some end-uses. For products used in the interior passenger compartment for automobiles, manufacturers often develop specifications on the level of emissions or "fog" which can be released as the automobile sits in the sun. Currently, no $C_8$ phthalate esters and no branched $C_9$ phthalate meet specifications which require a minimal fog formation observed after 3 hours at 100° C., in a fog testing apparatus. To meet these test performance criteria, phthalate esters of branched or linear $C_{10}$ and $C_{11}$ alcohols, phthalate esters of the more expensive linear $C_9$ alcohols or esters of trimellitic anhydride must be used.

In accordance with Wadey et al., "The Nonyl Phthalate Ester and Its Use in Flexible PVC", Journal of Vinyl Technology, December 1990, Vol. 12, No. 4, pp. 208–211, there are currently known various di-nonyl, di-2-methyloctyl (alpha branched) phthalate esters varying in degree of branching which are not yet commercially available. These include moderately branched phthalate esters (Jayflex DINP), slightly branched (Palatinol N), highly branched (3,5,5-trimethyl hexyl phthalate type), and linear $C_9$ phthalate (70% n-nonyl, 30% various alpha branched isomers).

It is known in the industry that typical branched $C_9$ phthalates fail the automotive fogging specifications. The present inventors have demonstrated in the examples set forth hereafter that the novel branched $C_7$–$C_{11}$ phthalate, trimellitate and adipate esters (e.g., branched $C_9$ phthalate, trimellitate and adipate esters) of the present invention which are formed from a branched oxo $C_7$–$C_{11}$ oxo alcohols unexpectedly pass the fog test. The branched nature of these plasticizers will make them slightly more compatible than conventional Jayflex L9P, and thus yield even better performance in PVC compounds. These unique branched $C_7$–$C_{11}$ oxo phthalate, trimellitate and adipate esters have low fogging properties which are highly desirable for use in automotive interior applications.

Phthalate esters prepared from branched $C_7$–$C_{11}$ oxo alcohols according to the present invention produce a flexible PVC plasticizer which has all the performance advantages associated with conventional branched $C_9$ phthalate esters, while dry-blending faster, i.e., process faster, than DOP. When compared to other known branched phthalate esters, the phthalate esters of branched $C_9$ oxo alcohols according to the present invention provide improved efficiency, better low temperature performance, and lower emission release (i.e. fogging) during processing.

Additionally, the present inventors have discovered that trimellitate esters formed according to the present invention tend to dry-blend faster than Jayflex TINTM (triisononyl trimellitate prepared from 3 moles of $C_9$ alcohol and 1 mole of trimellitic anhydride). They also tend to be more efficient. The trimellitate oxo esters according to the present invention may also replace TOTM (tri-2-ethyl hexyl trimellitate) in automotive instrument applications and in wire and cable formulations where conventional trimellitate esters have not been successful. Furthermore, because trimellitate oxo esters of the present invention have lower volatility, they will have a longer useful product life. Moreover, the trimellitate oxo esters could be used in fixture 125° C. wire applications where low volatility, higher plasticizer efficiency, and improved processability are desired.

The present invention also provides many additional advantages that shall become apparent as described below.

SUMMARY OF THE INVENTION

The present invention includes a novel series of plasticizer esters and method for making such ester for use in the formulation of polyvinyl chloride (PVC), such as phthalates, adipates and trimellitates. The plasticizer esters according to the present invention are prepared by the reaction of at least one branched $C_7$–$C_{11}$ oxo alcohol prepared by hydroformylation from $C_6$–$C_{10}$ olefins comprising at least 50% methyl branching at the beta carbon with at least one acid and/or anhydride, in the presence of a catalyst.

The present invention also includes a process for preparing a plasticizer ester comprising: reacting a branched $C_7$–$C_{11}$ oxo alcohol prepared from $C_6$–$C_{10}$ olefins by hydroformylation with at least one acid and/or anhydride in the presence of a catalyst, wherein said olefins comprise at least 50% methyl branching at the beta carbon.

The present invention also includes a polyvinyl chloride resin composition comprising polyvinyl chloride and the plasticizer esters of the present invention and optionally, stabilizers, fillers and other well-known additives that are commonly used in the art. The polyvinyl chloride resin compositions can be used to prepare films, sheets or extruded, molded or cast products that are suitable for use in all areas of polyvinyl chloride applications.

Other and further objects, advantages and features of the present invention will be understood by reference to the following specification in conjunction with the annexed drawings, wherein like parts have been given like numbers.

DESCRIPTION OF THE PREFERRED EMBODIMENTS

Figure 1A:
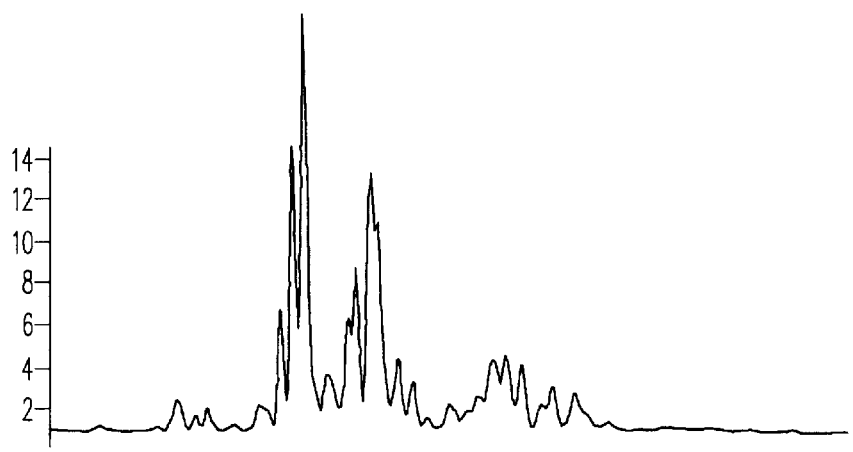
FIGS. 1a–1c are gas chromatograms of three conventional $C_9$ alcohols.

The plasticizer esters according to the present invention are prepared by esterification of acids and/or anhydrides with at least one branched $C_7$–$C_{11}$ oxo alcohol.

The esterification process comprises the following steps: (a) adding an excess of acid and/or anhydride and at least one branched $C_7$–$C_{11}$ oxo alcohol to a reaction vessel, provided that the olefin used to form the oxo alcohol comprises at least 50% methyl branching at the beta carbon; and (b) heating the reaction mixture to a temperature at about or above the boiling point of the oxo alcohol and maintaining a pressure sufficient to obtain boiling of the reaction mixture, thereby converting the acid and/or anhydride and the branched $C_7$–$C_{11}$ oxo alcohol to a phthalate, trimellitate or adipate ester and removing water and a portion of the alcohol from the reaction vessel.

The esterification process may further include one or more of the following steps: removing excess acid by nitrogen or steam stripping; adding adsorbents such as alumina, silica gel, activated carbon, clay and/or filter aid to the reaction mixture following esterification before further treatment; adding water and base to simultaneously neutralize the residual organic acids and to hydrolyze the catalyst (if present); filtering the solids from the ester mixture containing the bulk of the excess acid by steam or nitrogen stripping under vacuum and recycling of the acid into the reaction vessel; and removing solids from the stripped ester in a final filtration.

In certain cases, adsorbent treatment may occur later in the process following steam stripping. In other cases, the adsorbent treatment step may be eliminated from the process altogether.

Preferably, the plasticizer esters of the present invention are prepared by a metal or acid catalyzed reaction of an aromatic or aliphatic acid, such as a diacid, triacid, or the acid anhydrides thereof with an oxo alcohol prepared by the hydroformylation of $C_6$–$C_{10}$ olefins. According to the present invention, the olefin must contain at least 50% mono methyl branching at the beta carbon (e.g., 2-methyl octene-1 or 2-methyl octene-2 formed by the "oxo" process).

The preferred plasticizer esters are those that can be used for polyvinyl chloride resins. They include esters prepared from the reaction of an aliphatic oxo alcohol and an aromatic acid, wherein the aliphatic oxo alcohol is prepared by hydroformylation of an olefin mixture which includes at least 50% isomers having methyl substitution at the beta carbon. The aromatic acid is preferably selected from the group consisting of phthalic acid, trimellitic acid, anhydrides thereof, and mixtures thereof. The most preferred esters are those wherein the aromatic acid is phthalic anhydride or trimellitic anhydride and the aliphatic oxo alcohol is a branched $C_9$ oxo alcohol prepared by hydroformylation of 2-methyl octene-1 and/or 2-methyl octene-2.

Esterification Catalyst

The esterification process is preferably conducted in the presence of a catalyst. Typical esterification catalysts are titanium, zirconium and tin catalysts such as titanium, zirconium and tin alcoholates, carboxylates and chelates. See U.S. Pat. No. 3,056,818 (Werber) which issued on Oct. 2, 1962, and which is incorporated herein by reference.

Typical titanium alcoholates which can be used as catalysts include tetramethyl titanates, tetraethyl titanates, tetrapropyl titanates, tetra-isopropyl titanates, tetrabutyl titanates, tetrapentyl titanates, tetrahexyl titanates, tetraoctyl titanates, tetranonyl titanates, tetradodecyl titanates, tetrahexadecyl titanates, tetra-octadecyl titanates, tetradecyl titanates, tetraheptyl titanates and tetraphenyl titanates. The alkyoxy groups on the titanium atom can all be the same or they can be different. The zirconium counterparts of the above alcoholates can be substituted in whole or in part as catalysts.

The titanium carboxylates which serve as esterification catalysts are polymeric materials having at least one acyl group for each titanium atom. Typical titanium acylates which can be employed as catalysts include acylates from 2 to 18 carbon atoms, such as hydroxy titanium acetate, hydroxyl titanium butyrate, hydroxy titanium pentanoate, hydroxy titanium hexanoate, hydroxy titanium octanoate, hydroxy titanium decanoate, hydroxy titanium dodecanoate, hydroxy titanium tetradecanoate, hydroxy titanium hexadecanoate, hydroxy titanium octadecanoate, hydroxy titanium oleate, hydroxy titanium soya acylate, hydroxy titanium linseed acylate, hydroxy titanium castor acylate, hydroxy titanium tall oil acylate, hydroxy titanium coconut acylate, methoxy titanium acetate, ethoxy titanium butyrate, isopropoxy titanium pentanoate, butoxy titanium hexanoate, isopropoxy titanium octanoate, isopropoxy titanium decanoate, isopropyl titanium dodecanoate, isopropoxy titanium tetradecanoate, isopropoxy hexadecanoate, isopropoxy octadecanoate, isopropoxy titanium oleate, isopropoxy titanium soya acylate, isopropoxy linseed acylate, isopropoxy coconut acylate. The alkoxy group of the acylate can vary from 1 to 20 carbon atoms. The corresponding zirconium carboxylates can be used as catalysts.

Titanium chelates are formed by reacting a titanium compound with a polyfunctional molecule including polyols such as glycols or glycerine and amino alcohols, amino acids, hydroxy acids and polycarboxylic acids. Typical chelated esters which serve as catalysts include tetra-ethylene glycol titanate, tetrapropylene glycol titanate, tetrabutylene glycol titanate, tetra-octylene glycol titanate and tetrapolyethylene glycol titanate, dibutoxy di-(ethylene glycol) titanate, di-isopropoxy di-(octylene glycol) titanates, dimethoxy di-(octylene glycol) titanates, diethyoxy di-(octylene glycol) titanates, tetratriethanol amine titanate, tetratriethanol amine-N-oleate titanate, triethanol amine-N-stearate titanate, triethanol amine-N-linseed acid salt titanate, dibutoxy titanate, dipropoxy titanate, dimethoxy titanate, diethoxy titanate, other dialkoxy dipropoxy, dimethoxy, diethoxy titanates, and other dialkoxy di-(amino alcohol) titanates. The corresponding zirconium chelates are also useful as catalysts.

Selected acid catalysts may also be used in this esterification process. Some examples of acid catalysts are: sulfuric acid, benzene sulfonic acid, p-toluene sulfonic acid, naphthalene sulfonic acid, aluminum sulfate, aluminum powder, normal decylbenzene sulfonic acid, normal dodecylbenzene sulfonic acid, normal nonylbenzene sulfonic acid, normal octylbenzene sulfonic acid, normal heptylbenzene sulfonic acid, normal hexylbenzene sulfonic acid, normal tridecylbenzene sulfonic acid, normal tetradecylbenzene sulfonic acid, normal dodecane sulfonic acid, normal tridecane sulfonic acid, normal tetradecane sulfonic acid, normal pentadecane sulfonic acid, normal hexadecane sulfonic acid, normal heptadecane sulfonic acid, normal octadecane sulfonic acid, normal nonadecane sulfonic acid, normal eicosane sulfonic acid, 3-methyldodecane sulfonic acid, 3-methyl-5-ethyldecane sulfonic acid, 3-methyldecylbenzene sulfonic acid, 4-ethyloctylbenzene sulfonic acid, phosphoric acid, aromatic phosphonic acids (e.g., organic disulfonic acids, 1,2-ethanedisulfonic acid, 1,3-propanedisulfonic acid, m-benzene disulfonic acid, 2,5-, 2,6-, or 2,7-naphthalene disulfonic acids or mixtures of these isomers, and 3,5-o-xylenedisulfonic acid), acidic formalite resins prepared by reacting an aromatic hydrocarbon, an aldehyde, and sulfuric acid, methane disulfonic acid, methane trisulfonic acid, hydrochloric acid, perfluorinated resin sulfonic acid, acidic ion exchange resins, chlorosulfonic acid, thionyl chloride, boron trifluoride, dihydroxy fluoride, dihydroxy fluoboric acid, and silicon tetrafluoride.

Acids

Carboxylic acids which undergo esterification (i.e., mono or poly-basic acids, preferably dibasic or tribasic acids) can be aliphatic, cyclo-aliphatic or aromatic, they can be substituted or unsubstituted, saturated or unsaturated, or they can be blends of acids. Representative acids include acetic, hydroxyacetic, chloroacetic, bromoacetic, cyanoacetic, 5-phenylacetic, triphenyl acetic, propionic, halopropionic, lactic, beta-hydroxy propionic, n-butyric, isobutyric, n-valeric, isovaleric, 5-phenyl-n-valeric, n-heptanoic, caproic, pelargonic, caprylic, lauric, palmitic, lignoceric, alpha-hydroxy lignoceric, malonic, succinic, glutaric, adipic, pimelic, azelaic, sebacic, decane-1,10-dicarboxylic, pentadecane-1,15-dicarboxylic, pentacosane-1,25-dicarboxylic, 1,2,3-propane tricarboxylic, citric, acrylic, alpha-chloro acrylic, beta-chloro acrylic, beta-bromo acrylic, beta-phenyl acrylic, methacrylic, vinyl acetic, crotonic, angelic, tiglic, undecylenic, oleic, erucic, linoleic, linolenic, maleic, fumaric, mesaconic, citraconic, itaconic, mucconic, aconitic, myristic, stearic, isostearic, branched $C_5$ and $C_{10}$ (e.g., 3,5,5-trimethylhexanoic) and branched $C_{17}$, $C_{19}$, $C_{21}$, etc., acids.

Among the alicyclic acids are cyclopropane carboxylic, cyclobutane carboxylic, cyclopentane carboxylic, cycloheptane carboxylic, cyclohexane carboxylic, 2-hydroxy cyclohexane carboxylic, 1,1-cyclopropane dicarboxylic, 1,2-cyclobutane dicarboxylic, 1,3-cyclobutane dicarboxylic, 1,4-cyclohexane dicarboxylic, cyclohexane-1,2,3,4,5,6-hexacarboxylic, cyclopentene-2-carboxylic, 1-cyclohexene-1-carboxylic, hydrocapric, cyclohexadiene-1,2-dicarboxylic, and 1,3-cyclohexadiene-1,4-dicarboxylic.

The aromatic acids include benzoic, o-, m- and p-chloro and bromo benzoic, o-, m- and p-hydroxy benzoic, o-, m- and p-nitrobenzoic, o-, m- and p-methoxy benzoic, alpha-napthoic, beta-naphthoic, o-, m- and p-methyl benzoic, o-, m- and p-ethyl benzoic, p-phenyl benzoic, phthalic, isophthalic, terephthalic, hydroxy phthalic, 2,3-dimethyl benzoic, benzene-1,2,4-tricarboxylic, benzene-1,3,5-tricarboxylic, benzene-1,2,4,5-tetracarboxylic, diacids of naphthalenes and trimellitic.

Anhydrides

Anhydrides of mono- and poly-basic acids can be used in place of the acids, especially when plasticizer esters are being formed. These include acetic anhydride, propionic anhydride, n-butyric anhydride, succinic anhydride, glutaric anhydride, adipic anhydride, pimellic anhydride, maleic anhydride, mesaconic anhydride, citraconic anhydride, glutaconic anhydride, itaconic anhydride, phthalic anhydride, benzoic anhydride, nadic anhydride, methyl nadic anhydride, hexahydrophthalic anhydride, trimellitic anhydride and mixed anhydrides of monobasic acids. Another anhydride is pyromellitic dianhydride.

Alcohols

Among the alcohols which can be reacted with acids and anhydrides are $C_7$–$C_{11}$ oxo alcohols derived from branched $C_6$–$C_{10}$ olefins, such as 2-methyl octene-1 and 2-methyl octene-2 via the oxo process.

Among the monohydric alcohols which can be reacted with acids and anhydrides according to the present invention are, by way of example, most primary $C_7$–$C_{11}$ monohydric, substituted or unsubstituted alkanols and alkenols, such as, 3-methyl octanol and 7-methyloctanol.

The term "iso" is meant to convey a multiple isomer product made by the oxo process. It is desirable to have a branched oxo alcohol comprising multiple isomers, preferably at least two isomers.

Branched oxo alcohol may be produced in the so-called "oxo" process by hydroformylation of commercial branched $C_6$–$C_{10}$ olefin fractions to a corresponding branched $C_7$–$C_{11}$ alcohol-containing oxonation product, followed by conversion of the crude oxo alcohol-containing oxonation product to an oxo alcohol.

In order to produce oxo alcohol commercially, the hydroformylation process is adjusted to maximize oxo alcohol formation. This can be accomplished by controlling the temperature, pressure, catalyst concentration, and/or reaction time. Thereafter, the demetalled crude alcohol-containing oxonation product is hydrogenated to convert residual oxo aldehydes to oxo alcohols.

The production of branched oxo alcohols from the cobalt catalyzed hydroformylation of an olefinic feedstream preferably comprises the following steps:

(a) hydroformylating an olefinic feedstream by reaction with carbon monoxide and hydrogen (i.e., synthesis gas) in the presence of a hydroformylation catalyst under reaction conditions that promote the formation of an alcohol-rich crude reaction product;

(b) demetalling the alcohol-rich crude reaction product to recover therefrom the hydroformylation catalyst and a substantially catalyst-free, alcohol-rich crude reaction product;

(c) separating the catalyst-free, alcohol-rich crude reaction product into a concentrated alcohol-rich product and an alcohol-poor product; and (d) hydrogenating the concentrated alcohol-rich product, thereby forming an oxo alcohol.

The olefinic feedstream is preferably any $C_6$ to $C_{10}$ olefin, more preferably a branched $C_8$ olefin. Moreover, the olefinic feedstream is preferably a branched olefin, wherein at least 50% of the methyl branching occurs at the beta carbon atom. The hydroformylation and subsequent hydrogenation of the reaction of crude hydroformylation product is capable of producing branched $C_7$ to $C_{11}$ alcohols, more preferably branched $C_9$ oxo alcohol. Each of the branched oxo $C_7$ to $C_{11}$ alcohols typically comprises, for example, a mixture of branched oxo alcohol isomers, e.g., branched $C_9$ oxo alcohol comprises 2-methly octene-1 and 2-methyl octene-2.

The performance of several $C_9$ phthalate esters have been compared to the performance of the $C_9$ phthalate ester of the present invention that is prepared from branched $C_9$ oxo alcohol made from 2-methyl octene-1 and 2-methyl octene-2 via the oxo process, provided that at least 50% of the olefins have methyl branching at the beta carbon atom. The phthalate ester of the present invention demonstrated certain performance advantages in several key areas over both Jayflex® DINP and Palatinol® N, which are two commercial phthalate esters that are also derived from branched $C_9$ alcohol. Jayflex® DINP is prepared from a mixture which is predominantly dimethyl heptanols and trimethyl hexanols. Palatinol® N is prepared from a mixture of methyl octanols and dimethyl heptanols prepared by hydroformylation of dimerized butenes. A branched $C_9$ oxo alcohol was prepared from a mixture of 2-methyl octene-1 and 2-methyl octene-2 having the isomer distribution set forth below in TABLE 1. This table was developed from alcohol isomer and compositional data predicted based on known oxo selectivity model studies carried out on selected olefins. This data is based on the assumption that 2-methyl octene-1 and 2-methyl octene-2 will exhibit the same selectivity in the oxo process. If the selectivity is different, then the percentages reported for 3-methyl octanol and 7-methyl octanol in TABLE 1 could be reversed.

TABLE 1

PREDICTED COMPOSITIONS OF THE BRANCHED $C_9$ OXO ALCOHOL

| Compound | Percent |
| --- | --- |
| 1-nonanol | 6.4 |
| 2-methyl octanol | 2.4 |
| 2-ethyl heptanol | 0.8 |
| 2-propyl hexanol | 0.3 |
| 2-butyl pentanol | 0.1 |
| 3-methyl octanol | 42.3 |
| 7-methyl octanol | 27.9 |
| 2,6-dimethyl heptanol | 13.5 |
| 2-ethyl-5-methyl hexanol | 3.6 |
| 2,2-dimethyl heptanol | 0.9 |
| 2-isopropyl hexanol | 0.9 |
| 2-secbutyl pentanol | 0.9 |

Figure 1B:
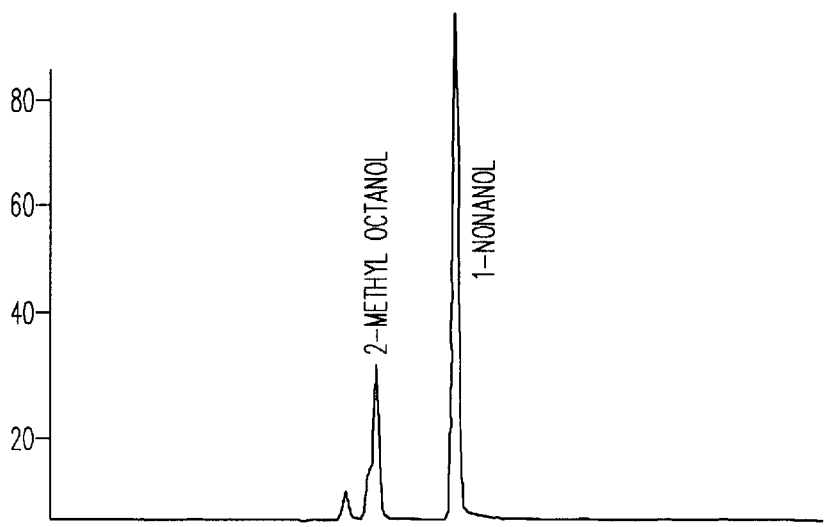
Figure 1C:
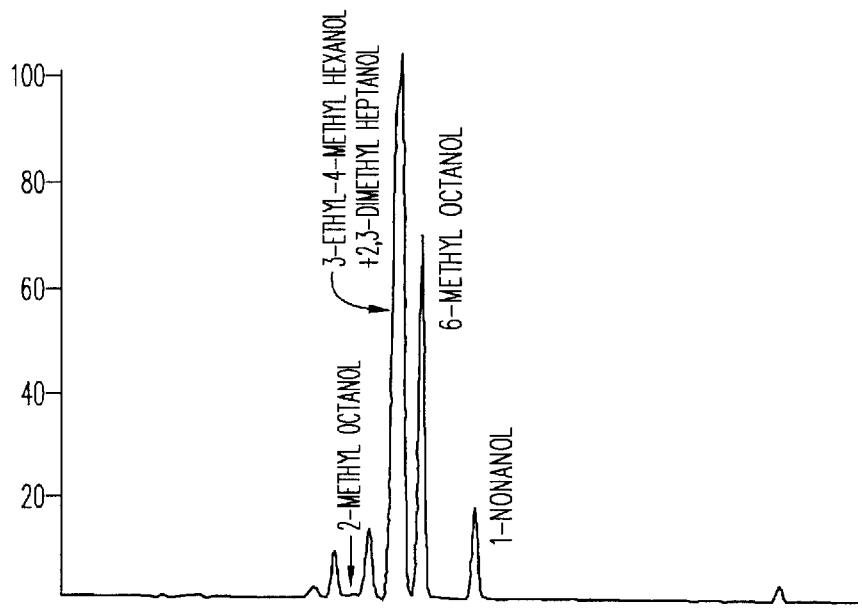
Figure 2:
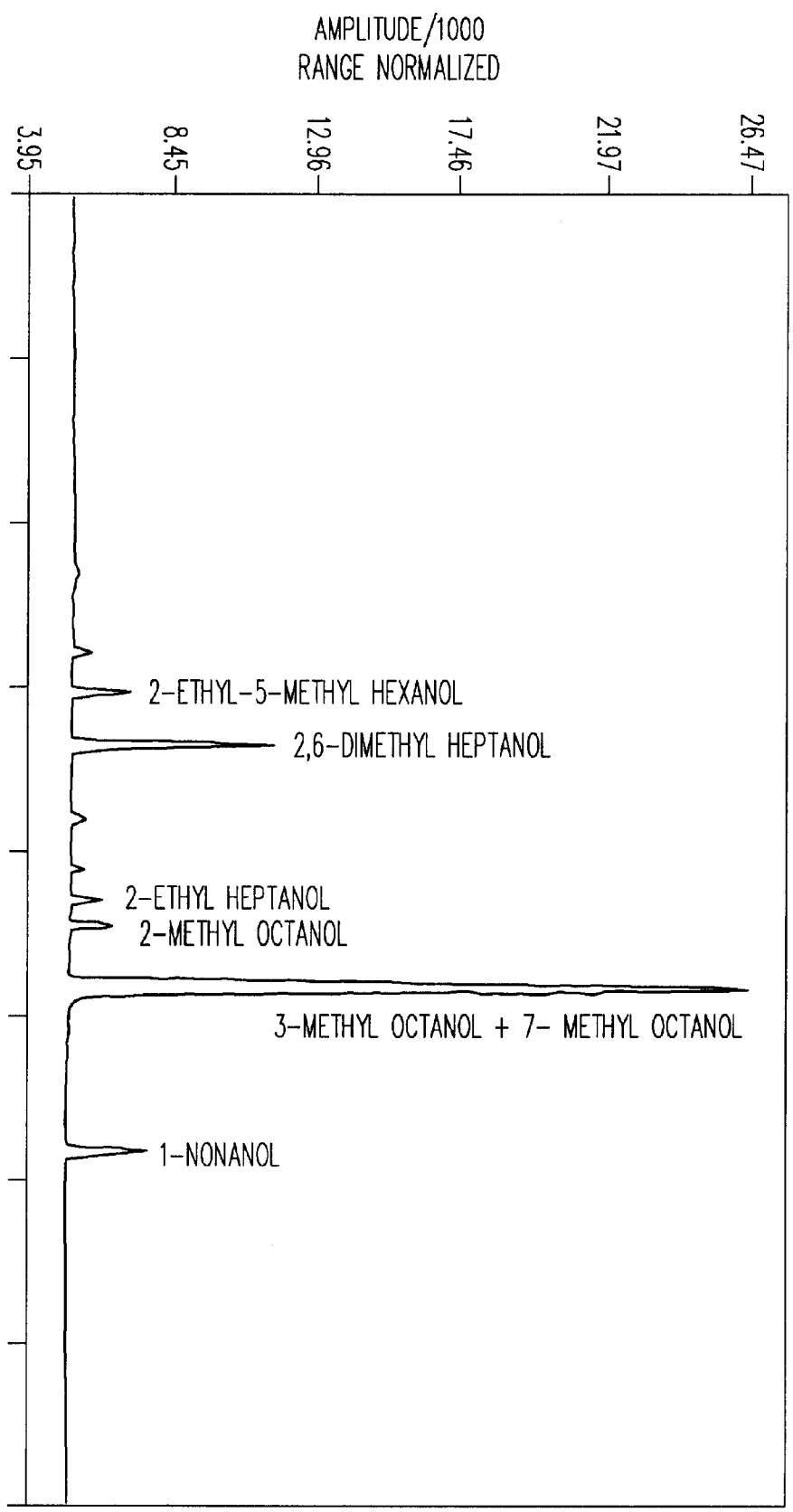
FIG. 2 is a theoretical gas chromatogram of the branched $C_9$ oxo alcohol formed according to an oxo process.

Gas chromatographic data for three $C_9$ alcohols, i.e., (1) branched $C_9$ oxo alcohol (isononyl alcohol, dimethyl heptanols and trimethyl hexanols); (2) slightly branched, linear $C_9$ alcohol, (i.e., a mixture of 65–75% n-nonanol, with smaller quantities of 2-methyl octanol, 2-ethyl heptanol, and 2-propyl hexanol (Jayflex L9P); and (3) slightly branched $C_9$ alcohol prepared by hydroformylation of butene dimer (Palatinol N) are shown in FIG. 1. FIG. 2 depicts a theoretical GC chromatogram for the branched $C_9$ oxo alcohol according to the present invention (i.e., with different retention time scale).

It has been discovered that the 2-methyl and the 6-methyl heptanols had the same retention times. It is assumed that 2-methyl and 7-methyl octanols will likewise have the same retention times. Unexpectedly, the branched $C_9$ oxo alcohol's GC pattern was different from the GC patterns of other known $C_9$ alcohols.

Table 2 lists a branching summary of the three reference alcohols compared to the value for the branched $C_9$ oxo alcohol formed in accordance with the present invention. The branching index refers to the number of branches per average molecule. The branched $C_8$ olefin derived alcohol of the present invention, with a composite branch index of 1.1 is significantly lower than that reported for the slightly branched C9-based alcohol. This reduced branching translates into some notable performance differences. Plasticizer viscosity for the phthalate ester of the present invention is found to be between that of Palatinolϕ N (i.e., a slightly branched $C_9$ phthalate ester) and Jayflex® L9P (i.e., a linear $C_9$ phthalate).

TABLE 2

$C_9$ ALCOHOL DATA

| | Slightly Branched $C_9$ | | Branched Octenes | |
| --- | --- | --- | --- | --- |
| | $C_9$[a] Palatinol N | SPA $C_9$ Jayflex DINP | LAO $C_9$ Jayflex L9P | $C_9$[b] Oxo Alcohol |
| Alcohol Branching | | | | |
| % Straight chain | 4 | <1 | 72 | 6 |
| % Mono-branched | 50 | 15 | 28 | 74 |
| % Di-branched | 44 | 66 | <1 | 20 |
| % Tri-branched | 2 | 18 | <1 | <1 |
| Branching index | 1.44 | 2.01 | 0.28 | 1.14 |
| Plasticizer | | | | |
| vis. @ 20° C., cSt | 80 | 100 | 54 | 67 |
| Plasticizer sp. gr. | 0.975 | 0.973 | 0.969 | 0.976[c] |

[a]BASF data for Dimersol $C_9$ alcohol
[b]Predicted
[c]Comparison with Palatinol N and Jayflex DINP data only Moreover, esterification of phthalic anhydride with the branched $C_9$ oxo alcohol of the present invention demonstrated similar reactivity to that of the conventional $C_9$ primary alcohols; whereas no quality problems with the phthalate ester are anticipated.

The COPPCO database, which is a computer model used to predict plasticizer performance in flexible PVC, contains plasticizer performance information about four $C_9$ phthalates: Jayflex DINP, Jayflex L9P, Palatinol® N, and a di-n-nonyl phthalate. COPPCO performance predictions for these phthalates (at 50 phr) as well as that for Palatinol® 711P are listed in Table 3. This data shows that, as the branching index decreases, plasticizer efficiency increases, low temperature performance increases, and the weight loss observed with oven aging and soapy water extraction decreases. These observations are consistent with that set forth in Wadey et al., "The Nonyl Phthalate Ester and Its Use in Flexible PVC", Journal of Vinyl Technology, December 1990, Vol. 12, No. 4, pg. 642. The performance of the isooctene-derived phthalate ester according to the present invention (i.e., Iso-$C_9$ DINP) is estimated through correlation of the plasticizer performance of these $C_9$ phthalates with branching index. This data is also displayed in Table 3.

TABLE 3

COPPCO Performance of $C_9$ Phthalate Esters in Flexible PVC

| Property | Jayflex DINP[a] | Palatinol 711P | Palatinol N | Jayflex L9P | DI-n-C9P | Iso-$C_9$ DINP[b] |
| --- | --- | --- | --- | --- | --- | --- |
| Shore A hardness | 84 | 81 | 83 | 80 | 80 | 82 |
| Shore D hardness | 31 | 29 | 30 | 28 | 27 | 29 |
| 100% modulus, N/mm² | 12.5 | 11.8 | 11.8 | 10.7 | 10.8 | 11.5 |
| Elongation. % | 329 | 342 | 365 | 335 | 332 | 335 |
| Clash-Berg $T_f$ ° C. | −24 | −32 | −26 | −33 | −36 | −28 |
| Brittleness Temp, ° C. | −32 | 41 | 35 | −43 | −46 | −38 |
| Weight loss, % (7 d @ 100° C.) | 5.4 | 5.6 | 4.0 | 3.4 | 2.4 | 4.0 |
| Volatility, carbon black, % | 1.0 | 1.1 | 1.3 | 0.9 | 0.9 | 0.9 |
| Soapy water loss, % | 2.0 | 3.4 | 1.8 | 1.6 | 1.4 | 1.7 |
| Compound spec. gravity | 1.221 | 1.221 | 1.222 | 1.220 | 1.216 | 1.221 |
| Dry blend time, | 1.9 | 1.0 | 1.6 | 1.0 | 1.0 | 1.2 |

TABLE 3-continued

COPPCO Performance of $C_9$ Phthalate Esters in Flexible PVC

| Property | Jayflex DINP[a] | Palatinol 711P | Palatinol N | Jayflex L9P | DI-n-C9P | Iso-$C_9$ DINP[b] |
|---|---|---|---|---|---|---|
| minutes | | | | | | |

[a]COPPCO predicted values: PVC 100 parts, plasticizer 50 phr, stabilizer 2 phr
[b]Extrapolated data, from COPPCO data versus branching index (i.e., a plasticizer formed from branched $C_9$ oxo alcohol)

In terms of performance ranges, Palatinol N falls at mid range between Jayflex DINP and the isooctene derived DINP of the present invention. Isooctene derived DINP shows performance advantages over Palatinol N with higher efficiency, better low temperature performance, and reduced weight loss, but in a manufacturing environment these differences may be difficult to quantitative. However, the differences between Jayflex DINP and the isooctene derived DINP is statistically significant (but still less than the performance differences between DOP (di-2-ethylhexyl phthalate) and Jayflex DINP) in both the laboratory and manufacturing environment, with the isooctene derived plasticizer having several areas of improved plasticizer performance. Jayflex DINP is less efficient, which translates into a slight volume coat advantage, assuming that the specific gravity projections are correct and that the cost ratios between PVC resin and plasticizer are favorable.

Wadey's data shows that there are small differences between the performance of phthalate esters prepared from 1-nonanol phthalate and 2-methyl nonanol. Thus, it is to be expected that if a slightly branched, linear $C_9$ alcohol (i.e, a mixture of 65–75% n-nonanol, with smaller quantities of 2-methyl octanol, 2-ethyl heptanol and 2-propyl hexanol.) is blended with the branched $C_9$ oxo alcohol of the present invention, there will be a decrease in plasticizer performance. A 10% addition of the branched $C_9$ oxo alcohol to slightly branched, linear $C_9$ alcohol should give a 1° C. decrease in plasticizers low temperature performance. Other performance properties should be unaffected. Thus, it may be desirable to intentionally blend significant levels of slightly branched, linear $C_9$ alcohol with the branched $C_9$ oxo alcohol prior to esterification.

The present invention also includes a polyvinyl chloride resin composition comprising polyvinyl chloride and the plasticizer esters of the present invention. The plasticizer esters of the present invention are formed from the reaction of an aliphatic oxo alcohol and an aromatic acid, wherein the aliphatic oxo alcohol is prepared by hydroformylation of an olefin mixture, wherein the olefins comprise at least 50% methyl branching at the beta carbon.

The polyvinyl chloride resin composition comprises a polyvinyl chloride, typically unplasticized, in an amount from about 25–99.99 weight % of the composition and a plasticizer ester of the present invention in an amount from about 0.01–75 weight % of the composition.

The polyvinyl chloride resin formulation containing the unique plasticizers of the present invention are exemplified by the following basic formulations:

| Reactant | Ex. 1 | Ex. 2 |
|---|---|---|
| PVC (suspension grade, K 69), parts | 100 | — |
| PVC (dispersion grade, K 74), parts | — | 100 |
| Plasticizer, parts per hundred resin (phr) | 25, 35, 50 | 50, 70, 90 |
| Ba/Cd/Zn liquid stabilizer (phr) | 2.0 | 2.0 |
| Stearic acid (phr) | 0.25 | 0.25 |

The polyvinyl chloride resin composition can further comprise stabilizers, fillers and other well-known additives that are commonly used in the art. Preferably, the polyvinyl chloride resin composition comprises 0.01–7 weight % of a stabilizer selected from compounds of calcium, barium, cadmium, zinc, lead, and mixtures thereof; and/or 0.01–6 weight % of a filler selected from calcium carbonate, clay, and mixtures thereof.

The polyvinyl chloride resin composition of the present invention can be used to prepare films, sheet or an extruded, molded or cast products that are suitable for use in all areas of polyvinyl chloride applications. The molded or cast products of the present invention are particularly suitable for use in automotive applications such as automotive interior parts.

While we have shown and described several embodiments in accordance with our invention, it is to be clearly understood that the same are susceptible to numerous changes apparent to one skilled in the art. Therefore, we do not wish to be limited to the details shown and described but intend to show all changes and modifications that fall within the scope of the appended claims.

What is claimed is:

1. A process for preparing a plasticizer ester comprising: reacting a branched $C_7$–$C_{11}$ oxo alcohol prepared by hydroformylation of $C_6$–$C_{10}$ olefins with at least one acid and/or anhydride in the presence of a catalyst, wherein said olefins comprise at least 50% methyl branching at the beta carbon.

2. The process according to claim 1, wherein said alcohol is a branched $C_9$ oxo alcohol formed from 2-methyl octene-1 and/or 2-methyl octene-2.

3. The process according to claim 1, wherein said plasticizer ester is selected from the group consisting of: phthalate esters, adipate esters, trimellitate esters and mixtures thereof.

4. The process according to claim 1, wherein said acid or anhydride is selected from the group consisting of: diacids, triacids, anhydrides thereof and mixtures thereof.

5. A plasticizer ester prepared by the reaction of at least one branched $C_7$–$C_{11}$ oxo alcohol prepared by hydroformylation of $C_6$–$C_{10}$ olefins with at least one acid and/or anhydride, in the presence of a catalyst, wherein said olefins comprise at least 50% methyl branching at the beta carbon.

6. The plasticizer according to claim 5, wherein said alcohol is a branched $C_9$ oxo alcohol formed from 2-methyl octene-1 and/or 2-methyl octene-2.

7. The plasticizer according to claim 5, wherein said ester is selected from the group consisting of: phthalate esters, adipate esters, trimellitate esters and mixtures thereof.

8. The plasticizer according to claim 5, wherein said acid or anhydride is selected from the group consisting of: diacids, triacids, anhydrides thereof and mixtures thereof.

9. A plasticizer for polyvinyl chloride resin comprising an ester prepared from the reaction of an aliphatic oxo alcohol and an aromatic acid or anhydride, wherein said aliphatic oxo alcohol is prepared by hydroformylation of olefins, wherein said olefins comprise at least 50% methyl branching at the beta carbon.

10. The plasticizer according to claim 9, wherein said aromatic acid is selected from the group consisting of: phthalic acid, trimellitic acid, anhydrides thereof, and mixtures thereof.

11. The plasticizer according to claim 10, wherein said anhydride is phthalic anhydride and said aliphatic oxo alcohol is a branched $C_9$ oxo alcohol prepared by hydroformylation of 2-methyl octene-1 and/or 2-methyl octene-2.

12. The plasticizer according to claim 10, wherein said anhydride is trimellitic anhydride and said aliphatic oxo alcohol is a branched $C_9$ oxo alcohol formed from the hydroformylation of 2-methyl octene-1 and/or 2-methyl octene-2.

13. A polyvinyl chloride resin composition comprising polyvinyl chloride and a plasticizer, said plasticizer comprising an ester formed from the reaction of an aliphatic oxo alcohol and an aromatic acid or anhydride, wherein said aliphatic oxo alcohol is prepared by hydroformylation of olefin, wherein said olefins comprise at least 50% methyl branching at the beta carbon.

14. The polyvinyl chloride resin composition according to claim 13, wherein said polyvinyl chloride is present in an amount from about 25–99.99 weight %, based on the total weight of said composition and said plasticizer is present in an amount from about 0.01–75 weight %, based on the total weight of said composition.

15. The polyvinyl chloride resin compostion according to claim 13 further comprising:

0.01–7 weight % of a stabilizer selected from the group consisting of: calcium, barium, cadmium, zinc, lead, and mixtures thereof; and/or 0.01–6 weight % of a filler selected from the group consisting of: calcium carbonate, clay, and mixtures thereof.

16. A film, sheet or an extruded, molded or cast product prepared from the polyvinyl chloride resin composition of claim 13.

17. The product according to claim 16, wherein said molded or cast product is for use in automotive interior parts.

* * * * *